United States Patent
Rittner et al.

(10) Patent No.: US 9,119,976 B2
(45) Date of Patent: Sep. 1, 2015

(54) OXYGEN BREATHING DEVICE AND METHOD FOR MAINTAINING AN EMERGENCY OXYGEN SYSTEM

(75) Inventors: Wolfgang Rittner, Ahrensbok (DE); Rudiger Meckes, Berkenthin (DE)

(73) Assignee: Zodiac Aerotechnics, Plaisir (FR)

( * ) Notice: Subject to any disclaimer, the term of this patent is extended or adjusted under 35 U.S.C. 154(b) by 352 days.

(21) Appl. No.: 13/542,803

(22) Filed: Jul. 6, 2012

(65) Prior Publication Data
US 2014/0000590 A1    Jan. 2, 2014

Related U.S. Application Data

(60) Provisional application No. 61/665,486, filed on Jun. 28, 2012.

(51) Int. Cl.
| | | |
|---|---|---|
| A62B 7/00 | (2006.01) | |
| A62B 7/02 | (2006.01) | |
| A62B 7/08 | (2006.01) | |
| A62B 9/02 | (2006.01) | |
| A62B 18/00 | (2006.01) | |
| A62B 18/02 | (2006.01) | |
| A61M 16/20 | (2006.01) | |
| A62B 7/14 | (2006.01) | |
| A62B 21/00 | (2006.01) | |
| B64D 10/00 | (2006.01) | |

(52) U.S. Cl.
CPC .................. *A62B 7/08* (2013.01); *A61M 16/20* (2013.01); *A62B 7/00* (2013.01); *A62B 7/02* (2013.01); *A62B 7/14* (2013.01); *A62B 9/02* (2013.01); *A62B 18/02* (2013.01); *A62B 21/00* (2013.01); *B64D 10/00* (2013.01); *B64D 2231/00* (2013.01); *B64D 2231/02* (2013.01)

(58) Field of Classification Search
CPC ..... G05D 11/00; G05D 16/20; G05D 7/0629; G05D 23/12; F16K 7/17; A62B 7/08; A62B 7/00; A62B 7/02; A62B 7/04; A62B 7/06; A62B 7/14; A61M 16/20; A61M 16/201; A61M 16/202; A61M 16/203; A61M 16/00
USPC ............. 128/202.26, 200.24, 201.23, 201.28, 128/205.11, 205.15, 204.18, 204.21, 128/204.29, 205.23, 205.24, 207.16; 137/601.18, 601.2, 81.1, 513.3, 517, 137/504; 138/46
See application file for complete search history.

(56) References Cited

U.S. PATENT DOCUMENTS 2,841,174 A * 7/1958 Frye ........................... 137/514.5
3,289,694 A * 12/1966 Elliott et al. ............. 137/533.13
(Continued)

FOREIGN PATENT DOCUMENTS

EP         2143469         1/2010

*Primary Examiner* — Justine Yu
*Assistant Examiner* — Tu Vo
(74) *Attorney, Agent, or Firm* — Kilpatrick Townsend & Stockton LLP; Dean W. Russell; Renae Bailey Wainwright

(57) ABSTRACT

The invention relates to an oxygen breathing device that includes an oxygen source, in particular a chemical oxygen generator or an oxygen pressure tank, at least one oxygen mask connected via an oxygen supply line to said oxygen source, and a flow control unit adapted to receive a signal indicating ambient pressure or to detect ambient pressure and to control the flow of oxygen through the oxygen supply line depending on said ambient pressure. In some embodiments, the flow control unit is adapted to provide a low oxygen flow at a first ambient pressure and provide a higher oxygen flow at a second ambient pressure which is lower than said first ambient pressure.

18 Claims, 7 Drawing Sheets

(56) References Cited

U.S. PATENT DOCUMENTS

| | | | |
|---|---|---|---|
| 4,209,491 A * | 6/1980 | Rich, III | 422/110 |
| 4,651,728 A * | 3/1987 | Gupta et al. | 128/201.28 |
| 6,742,540 B2 * | 6/2004 | Kim | 137/513.3 |
| 2003/0015238 A1 * | 1/2003 | Martin | 137/384 |
| 2010/0319698 A1 * | 12/2010 | Cannon | 128/204.21 |
| 2011/0174307 A1 * | 7/2011 | Lessi et al. | 128/204.21 |
| 2012/0097166 A1 * | 4/2012 | Libis et al. | 128/205.14 |

* cited by examiner

OXYGEN BREATHING DEVICE AND METHOD FOR MAINTAINING AN EMERGENCY OXYGEN SYSTEM

CROSS-REFERENCE TO RELATED APPLICATION

This application claims the benefit of U.S. Provisional Application No. 61/665,486 filed on Jun. 28, 2012, the contents of which are incorporated herein by reference.

BACKGROUND

The invention relates to an oxygen breathing device, comprising an oxygen source, in particular a chemical oxygen generator or an oxygen pressure tank, at least one oxygen mask connected via an oxygen supply line to said oxygen source, a flow control unit adapted to receive a signal indicating ambient pressure or to detect ambient pressure and to control the flow of oxygen through the oxygen supply line depending on said ambient pressure, wherein the flow control unit is adapted to provide a low oxygen flow at a first ambient pressure, provide a higher oxygen flow at a second ambient pressure which is lower than said first ambient pressure and to increase said oxygen flow in at least two steps, preferably to increase said oxygen flow constantly.

A further aspect of the invention is a method for providing oxygen to a passenger of an aircraft and a method for maintaining an emergency oxygen system of an aircraft.

Generally, emergency oxygen supply systems for passengers of an aircraft are known. Such systems are used to supply oxygen to passengers in case of a pressure drop within the cabin or other emergency or critical situations, where the oxygen present in the cabin of the aircraft is not sufficient for the vital functions of the passenger within said cabin.

An emergency oxygen breathing device is known from the European patent application EP 2 143 469 A1. According to this reference, an oxygen breathing device provides oxygen flow from an oxygen source to an oxygen mask of a passenger or crew member. The oxygen flow is controlled by a control unit to ensure that the passenger is supplied with an exact amount of oxygen. The control unit receives pressure signals corresponding to the ambient pressure from a pressure sensor and temperature signals corresponding to the oxygen temperature passing through the breathing device from a temperature sensor. Generally, with such a device, it is possible to supply an amount of oxygen to a passenger in an emergency case which ensures that the passenger receives enough oxygen for maintaining all vital functions.

One important aspect of such oxygen breathing devices, however, is the desire to reduce the weight and the size of such devices in order to reduce the overall weight of the aircraft and to provide additional space for entertainment systems or the like. This size and weight reduction, however, shall not effect a reduction of the time period of supply of oxygen to a passenger. Accordingly, it is an object of the invention to provide an emergency oxygen system for passengers of an aircraft with reduced size and weight.

A further aspect of existing known assistance systems is the need to periodically maintain these systems and to adapt them to enhanced requirements or regulations in the aircraft industry. In the course of such maintenance it is a desire to be able to improve existing known oxygen systems in order to save weight and or space or to improve the characteristics of such systems in order to adapt them to existing requirements or regulations. It is a further object of the invention to provide a method and device which allows improvement of existing maintenance procedures in an efficient way.

It is another object to install modern oxygen masks which provide for low oxygen consumption at heights between 15,000 and 30,000 feet. Therefore, the oxygen flow at these heights needs to be adapted accordingly.

These and other objects are achieved by an oxygen breathing device according to the introductory function having an oxygen source, in particular a chemical oxygen generator or an oxygen pressure tank, at least one oxygen mask connected via an oxygen supply line to said oxygen source, a flow control unit adapted to receive a signal indicating ambient pressure or to detect ambient pressure and to control the flow of oxygen through the oxygen supply line depending on said ambient pressure, wherein the flow control unit is adapted to provide a low oxygen flow at a first ambient pressure, provide a higher oxygen flow at a second ambient pressure which is lower than said first ambient pressure and to increase said oxygen flow in at least two steps, preferably to increase said oxygen flow constantly, wherein a bypass valve is arranged in the oxygen supply line and comprises a first flow path and a second flow path comprising a bypass channel in a parallel flow arrangement to said first flow path, wherein said bypass valve is adapted to direct the flow of oxygen through said first flow path at an ambient pressure above a predetermined level according to a first flow condition and direct the flow of oxygen through said second flow path at an ambient pressure below a predetermined level according to a second flow condition, wherein said first flow path has a smaller flow cross section than said second flow path.

The oxygen breathing device provides for a weight saving means for life support of passengers in an aircraft. The device can be integrated in existing oxygen breathing systems without the need to redesign such existing systems. Moreover, the oxygen breathing device according to the invention is adapted to be used for currently used oxygen masks providing reduced oxygen consumption. Thereby, a reduced overall system weight can be achieved.

Preferably, the first ambient pressure is a system pressure corresponding to an altitude of the aircraft below 30,000 feet, e.g. intermediate altitudes between 15,000 and 30,000 feet. Still further it is preferred that the second ambient pressure is a system pressure corresponding to an altitude of the aircraft above 30,000 feet. The term smaller flow cross section reflects the fact that a smaller amount of oxygen per unit time can flow through the first flow path compared to the second flow path.

DESCRIPTION

According to a first preferred embodiment, said first flow path comprises a calibrated orifice. Thereby, a predetermined maximum amount of oxygen flow to the passenger can be achieved. Preferably, the calibrated orifice can be a channel with a predetermined cross section which is arranged in the first flow path in a way that oxygen flowing through the first flow path has to flow through the calibrated orifice. Depending on the size of the cross section the maximum oxygen flow to a passenger or crew member can be adjusted.

If the amount of oxygen entering the bypass valve exceeds the amount of oxygen leaving the bypass valve at the outlet due to the calibrated orifice, the pressure in the oxygen supply line increases. This pressure increase can be utilized as a signaling condition for the bypass valve to switch to the second flow condition.

According to a further embodiment said first flow path consists of a flow through a calibrated orifice only and said second flow path consists of a flow through said bypass channel only or said bypass channel and said calibrated orifice. This provides for a flexible and reliable embodiment of oxygen supply to the passenger.

A further preferred embodiment is characterized in that said bypass valve comprises a first flow channel comprising an orifice with a predetermined cross-section and a second flow channel, wherein a spring biased valve member engages a valve seat and a pressure inside the oxygen supply line acting against said spring to switch the valve member to switch the bypass valve between said first and second flow condition. This provides for an automatic and pressure controlled way of switching the bypass valve between the first and second flow condition.

The spring biased valve member preferably comprises an adjustable spring comprising an adjustment screw which can be mounted in a housing of the bypass valve. By adjusting the screw, the load of the spring and, accordingly, the pressure inside the oxygen supply line which is sufficient for lifting the valve member can be adjusted.

In another preferred embodiment a plurality of oxygen masks are connected to said oxygen source via a manifold, the oxygen supply line comprises a first central oxygen line section directing oxygen from the oxygen source to said manifold and a plurality of second oxygen line sections each directing oxygen from the manifold to an oxygen mask, said bypass valve is arranged in flow direction between said flow control unit and said oxygen masks. This provides for a central supply of oxygen from the oxygen source to the plurality of oxygen masks.

In another embodiment said bypass valve is arranged in said first central oxygen line section, in particular in flow direction between said flow control unit and said manifold. This provides for further weight saving, since a centralized bypass valve is provided for a plurality of oxygen masks, i.e. for the oxygen supply of a plurality of passengers.

A further embodiment of the aforementioned oxygen breathing device comprises a plurality of bypass valves, wherein at least a number of said plurality of second oxygen line sections comprises one of said plurality of bypass valves. Thereby, a decentralized arrangement of the bypass valves is achieved which provides for an increased liability of the oxygen breathing device. If one of the bypass valves does not function sufficiently, which would lead to a malfunction of the oxygen supply to one of the oxygen masks, the other remaining oxygen masks will still work sufficiently. In such an emergency case two passengers are able to share one oxygen mask.

According to a further embodiment of the oxygen breathing device, said bypass valve comprises a first and a second calibrated orifice, said second calibrated orifice having a larger flow cross section than said first calibrated orifice, wherein in said first flow condition the oxygen is flowing through said first calibrated orifice and in said second flow condition the oxygen is at least partially circumventing said first calibrated orifice and is flowing through said second calibrated orifice. This provides for a predetermined maximum oxygen flow in the second flow condition. Thereby, the oxygen flow to the passenger breathing mask can be calibrated both for the first and second flow condition. Hence, there is no need for a further calibrated orifice arranged in the passenger breathing mask.

According to a further embodiment of the breathing device, in said second flow condition a first part of the oxygen is flowing through said first calibrated orifice and a second part of the oxygen is flowing through a bypass channel arranged in parallel to said first calibrated orifice.

According to another embodiment, in said first flow condition the oxygen is flowing through said first and second calibrated orifice in a serial arrangement. This provides for a space saving design of the bypass valve with a simplified design.

In another embodiment of the oxygen breathing device said bypass valve comprises a housing having an inlet opening and an outlet opening, a first flow channel connecting said inlet opening and said outlet opening, a second flow channel connecting said inlet opening and said outlet opening a valve piston sealing against a valve seat inside said housing, wherein, when said valve piston is in sealing contact to said valve seat, the second flow channel is interrupted thus requiring oxygen flowing through the bypass valve from the inlet to the outlet opening to flow through said first flow channel, and wherein, when said valve piston is in a distance position without contact to said valve seat, the second flow channel is open thus allowing oxygen flowing through the bypass valve from the inlet to the outlet opening to flow through said first and said second flow channel. Thereby, a reliable bypass valve with a simple design is achieved.

According to another embodiment of the aforementioned oxygen breathing device, a first calibrated orifice is arranged in the first flow channel and a second calibrated orifice is arranged in the second flow channel, wherein said first calibrated orifice has a smaller flow cross section than said second calibrated orifice. This provides for a oxygen flow to the passenger in the second flow condition which is greater than the oxygen flow to the passenger in the first flow condition.

According to a further embodiment of the aforementioned oxygen breathing device, said piston is hollow, the first and second flow channel extend through said piston and said second calibrated orifice is arranged in the piston. Thereby, a space saving design of the bypass valve is achieved.

A further aspect of the invention is a method for providing oxygen to a passenger of an aircraft, comprising the steps of:
providing oxygen from an oxygen source to at least one oxygen mask,
automatically controlling the oxygen by a flow control unit by
receiving a signal indicating ambient pressure or detecting ambient pressure and
controlling the flow of oxygen through the oxygen supply line depending on said ambient pressure, in that a low oxygen flow is provided at a first ambient pressure, and a higher oxygen flow is provided at a second ambient pressure which is lower than said first ambient pressure
whereby said oxygen flow is increased in at least two steps, preferably constantly,
characterized in that
the oxygen is directed from said flow control unit to said oxygen mask via a bypass valve comprising a first flow path and a second flow path comprising a bypass channel in a parallel flow arrangement to said first flow path,
switching said bypass valve to
direct the flow of oxygen through said first flow path at an ambient pressure above a predetermined level according to a first flow condition and
direct the flow of oxygen through said second flow path at an ambient pressure below a predetermined level according to a second flow condition,
wherein said first flow path has a smaller flow cross section than said second flow path.

Another aspect of the invention is a method for maintaining an emergency oxygen system of an aircraft, said emergency oxygen system comprising:

an oxygen source, in particular a chemical oxygen generator or an oxygen pressure tank,
at least one oxygen mask connected via an oxygen supply line to said oxygen source,
a flow control unit adapted to receive a signal indicating ambient pressure or to detect ambient pressure and to control the flow of oxygen through the oxygen supply line depending on said ambient pressure, wherein the flow control unit is adapted to
provide a low oxygen flow at a first ambient pressure,
provide a higher oxygen flow at a second ambient pressure which is lower than said first ambient pressure and
to increase said oxygen flow in at least two steps, preferably to increase said oxygen flow constantly,
characterized by the steps of
installing a bypass valve in said oxygen supply line, said bypass valve comprising a first flow path and a second flow path comprising a bypass channel in a parallel flow arrangement to said first flow path, wherein said bypass valve is adapted to
direct the flow of oxygen through said first flow path at an ambient pressure above a predetermined level according to a first flow condition and
direct the flow of oxygen through said second flow path at an ambient pressure below a predetermined level according to a second flow condition,
wherein said first flow path has a smaller flow cross section than said second flow path.

DESCRIPTION OF THE DRAWINGS

Preferred embodiments of the invention are described in connection with the figures, wherein

FIG. 1 shows a bypass valve 1 arranged in an oxygen supply line 2 comprising a first flow path 3 and a second flow path 4. The bypass valve 1 can preferably be positioned in oxygen flow direction close to a passenger oxygen mask not shown in FIG. 1. The second flow path 4 comprises a bypass channel 5 in a parallel flow arrangement to the first flow path 3. The bypass valve 1 is adapted to direct a flow of oxygen 6 through said first flow path 3 at an ambient pressure above a predetermined level, according to a first flow condition, i.e. a system pressure corresponding to an altitude of the aircraft below 30,000 feet. Therefore, at intermediate altitudes, e.g. 15,000-30,000 feet, the second flow path 4 of the bypass valve 1 is closed.

Figure 1:
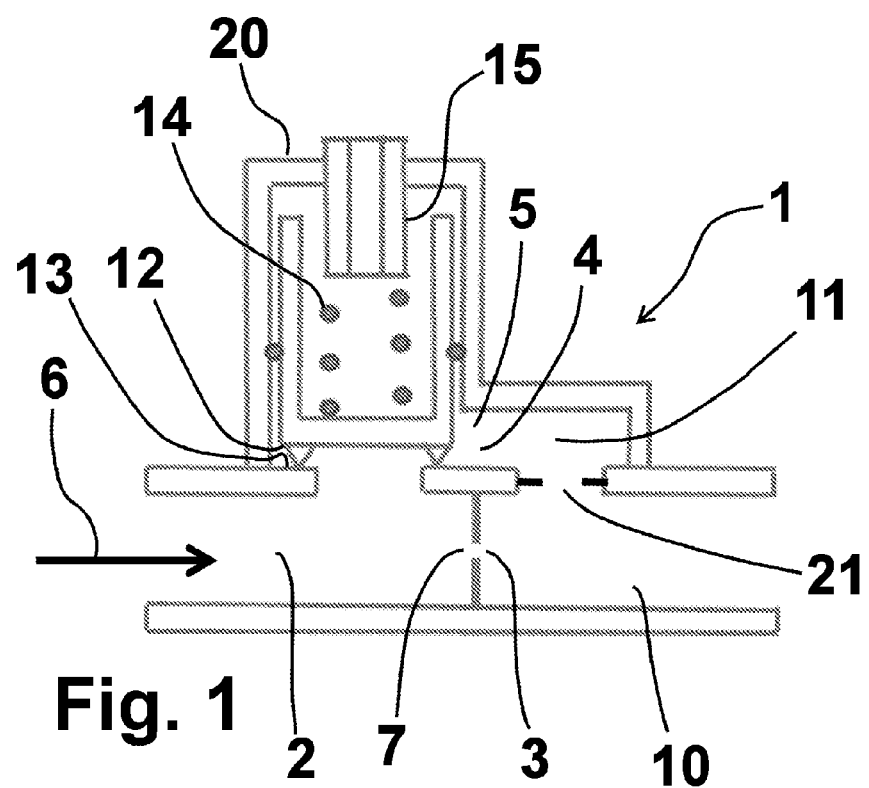
FIG. 1 is a schematic representation of a first embodiment of a bypass valve in a side view, shown in a closed position, according to the present invention.
Figure 1A:
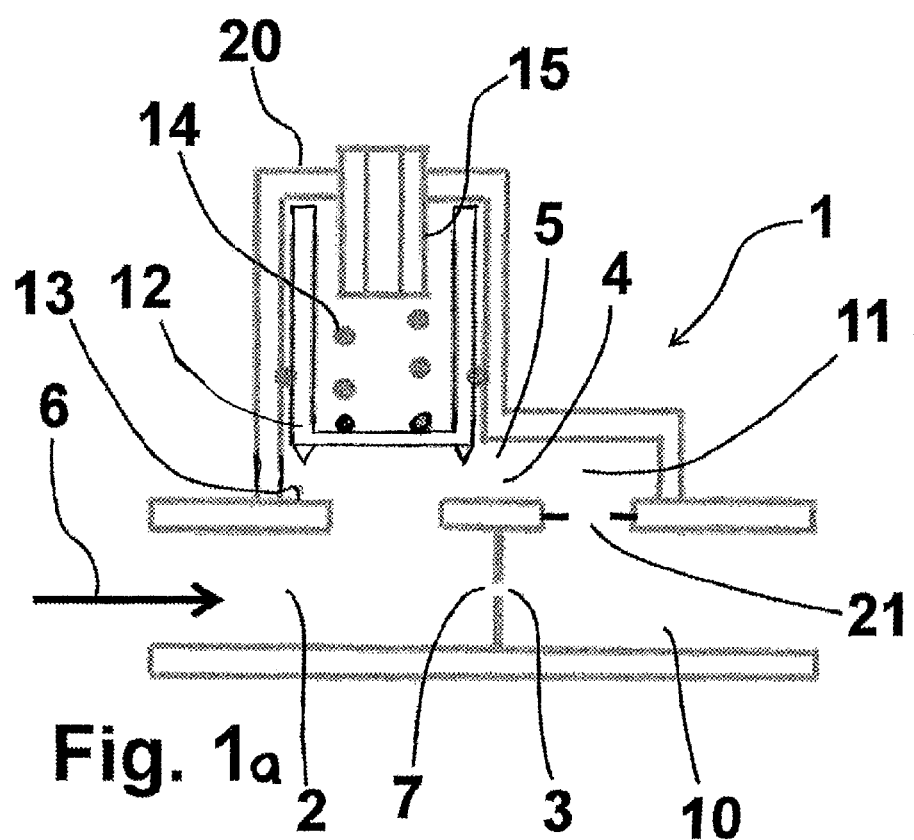
FIG. 1a is a schematic representation of the first embodiment of the bypass valve of FIG. 1 in a side view, shown in an open position, according to the present invention.

Furthermore, the bypass valve 1 is adapted to direct the flow of oxygen 6 through said second flow path 4 at an ambient pressure below a predetermined level according to a second flow condition, i.e. a system pressure corresponding to an altitude of the aircraft above 30,000 feet. The first flow path 3 comprises a calibrated orifice 7 which has a smaller flow cross section than the second flow path 4 when it is open. At intermediate altitudes, the calibrated orifice 7 reduces the effective flow of oxygen to the passenger mask.

The bypass valve 1 comprises a first flow channel 10 which serves as the first flow path 3. The second flow path 4 consists of a second flow channel 11, wherein a spring biased valve member 12 contacts a valve seat 13 when the second flow path 4 is closed. A pressure inside the oxygen supply line 2 acts against a spring 14 to engage the valve member 12 to switch the bypass valve 1 between a first and second flow condition. I.e. the orifice 7 is calibrated in a way that at a predetermined inlet pressure, the valve member 12 will be lifted against the force of the spring 14. Thereby, the second flow path 4 is opened.

The load of the spring 14 can be adjusted by an adjustment screw 15 which is mounted in a housing 20 of the bypass valve 1. In an alternative embodiment of the bypass valve 1, the design of the valve member 12 can also be realized by a membrane arrangement. The second flow channel 11 comprises a calibrated orifice 21 with a cross section which is greater than the cross section of the calibrated orifice 7.

Figure 2:
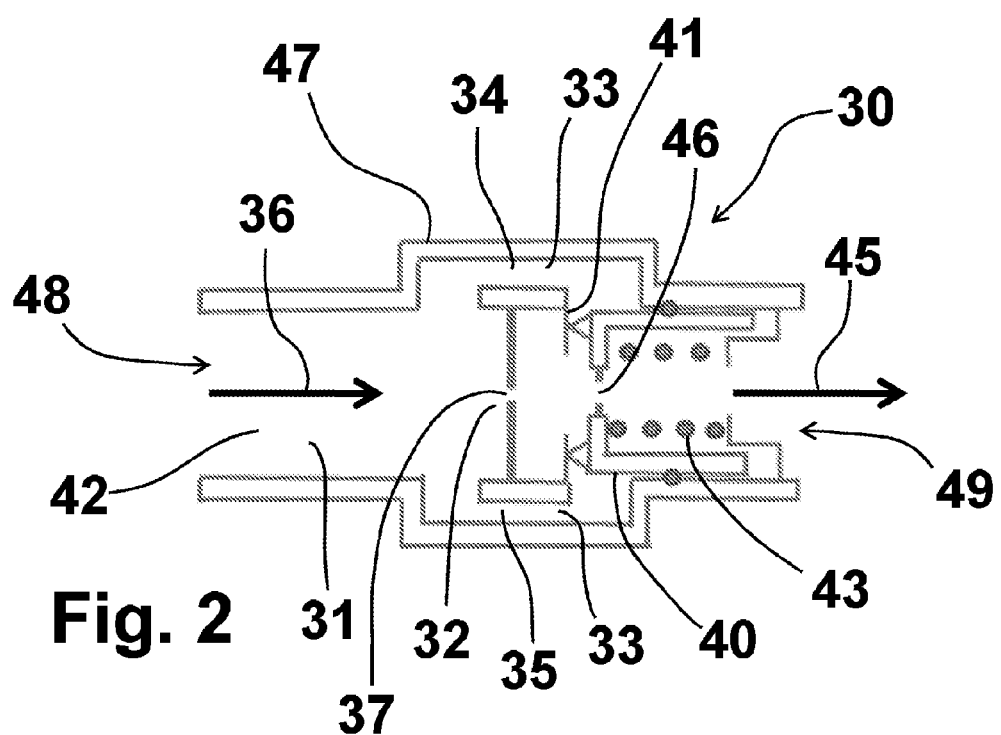
FIG. 2 is a schematic representation of a second embodiment of a bypass valve in a side view, shown in a closed position, according to the present invention.
Figure 2A:
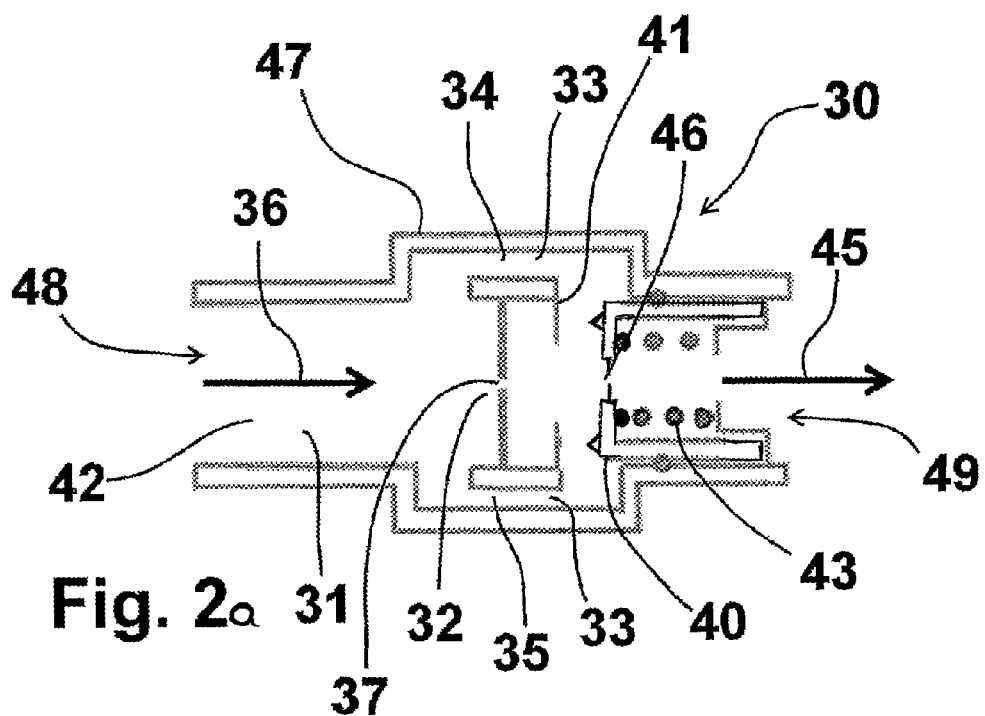
FIG. 2a is a schematic representation of the second embodiment of the bypass valve of FIG. 2 in a side view, shown in an open position, according to the present invention.

FIG. 2 shows a bypass valve 30 arranged in an oxygen supply line 31 comprising a first flow channel 32 and a second flow channel 33. The second flow channel 33 comprises two bypass channels 34 and 35 in a parallel flow arrangement to the first flow channel 32. The bypass valve 30 is adapted to direct a flow of oxygen 36 through said first flow channel 32 at an ambient pressure above a predetermined level, i.e. a system pressure corresponding to an altitude of the aircraft below 30,000 feet.

The first flow channel 32 comprises a calibrated orifice 37 which provides for a certain flow of oxygen at a certain pressure in an inlet 42 of the bypass valve 30.

In flow direction behind the calibrated orifice 37 the bypass valve 30 comprises a piston 40 with a valve seat 41 which is closed when the oxygen pressure in the inlet 42 of the bypass valve is lower than a predetermined pressure value. The piston 40 will be lifted against a force of a spring 43 when the inlet pressure exceeds the predetermined value. The load of the spring 43 can be adjusted by an adjustment screw not shown in FIG. 2 which is mounted in a housing 47 of the bypass valve 30. Then oxygen flows through the first flow channel 32 and, additionally, through the second flow channel 33, i.e. through the bypass channels 34 and 35. Thereby, an increased oxygen flow 45 is achieved at an outlet 46 of the bypass valve 30 adapted to direct the oxygen flow 45 to a passenger oxygen mask not shown in FIG. 2.

The piston 40 is a hollow and a second calibrated orifice 46 is arranged in the piston 40 in oxygen flow direction behind the first and second flow channel 33. The bypass valve 30 is encapsulated by the housing 47 comprising an inlet opening 48 and an outlet opening 49. Oxygen flowing from the inlet opening 48 to the outlet opening 49 passes through orifice 37 and further through orifice 46 in a first flow condition. The orifice 46 has a greater cross section than orifice 37. In a second flow condition, oxygen flowing from the inlet opening 48 to the outlet opening 49 passes through the orifice 37, additionally through the channels 34 and 35 and then through the orifice 46.

Figure 3:
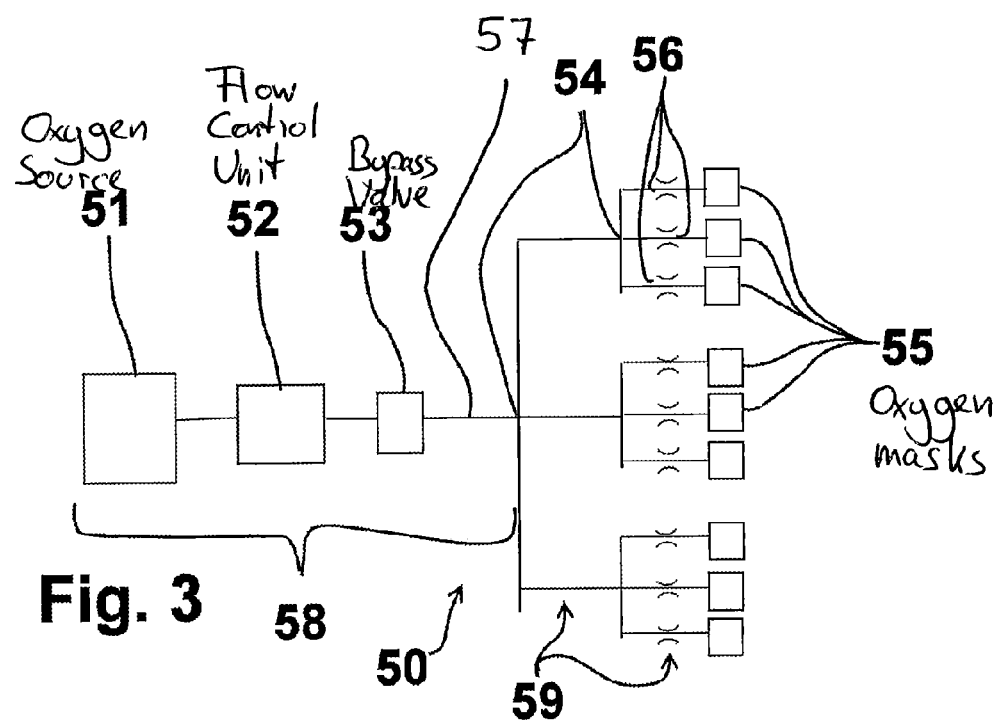
FIG. 3 is a first embodiment of an oxygen breathing device in a schematic view according to the present invention.

FIG. 3 shows a first embodiment of an oxygen breathing device 50 in a schematic view comprising an oxygen source 51. The oxygen source 51 can be a high pressure gaseous oxygen or chemical oxygen source. The pressurized oxygen supplied by the oxygen source 51 enters a flow control unit 52 including a regulation valve. The flow control unit 52 controls the outlet pressure of the oxygen flow to be supplied to a bypass valve 53 arranged in flow direction behind the flow control unit 52. The flow control depends on the altitude of the aircraft, i.e. the flow control unit 52 receives a signal indicating ambient pressure and controls the oxygen flow accordingly. Preferably, the outlet pressure of the flow control unit 52 is a suitable system and/or breathing pressure. With increased altitude the flow control unit 52 increases the oxygen pressure to be supplied to the bypass valve 53. The bypass valve 53 can be a bypass valve substantially equal to the bypass valve as described in FIG. 1.

The oxygen breathing device 50 further comprises a distribution network with manifolds 54 for distributing the oxygen flow to a number of passenger oxygen masks 55. Calibrated orifices 56 are arranged close to the oxygen passenger masks 55 in oxygen flow direction close to each oxygen mask 55. The oxygen source 51, the flow control unit 52, the bypass valve 53 and the oxygen masks 55 are connected via an oxygen supply line 57. The oxygen supply line 51 includes a first central oxygen line section 58 directing oxygen from the oxygen source 51 to the manifold 54 and a plurality of second oxygen line sections 59 each directing oxygen from the manifold 54 to an oxygen mask 55.

Figure 4:
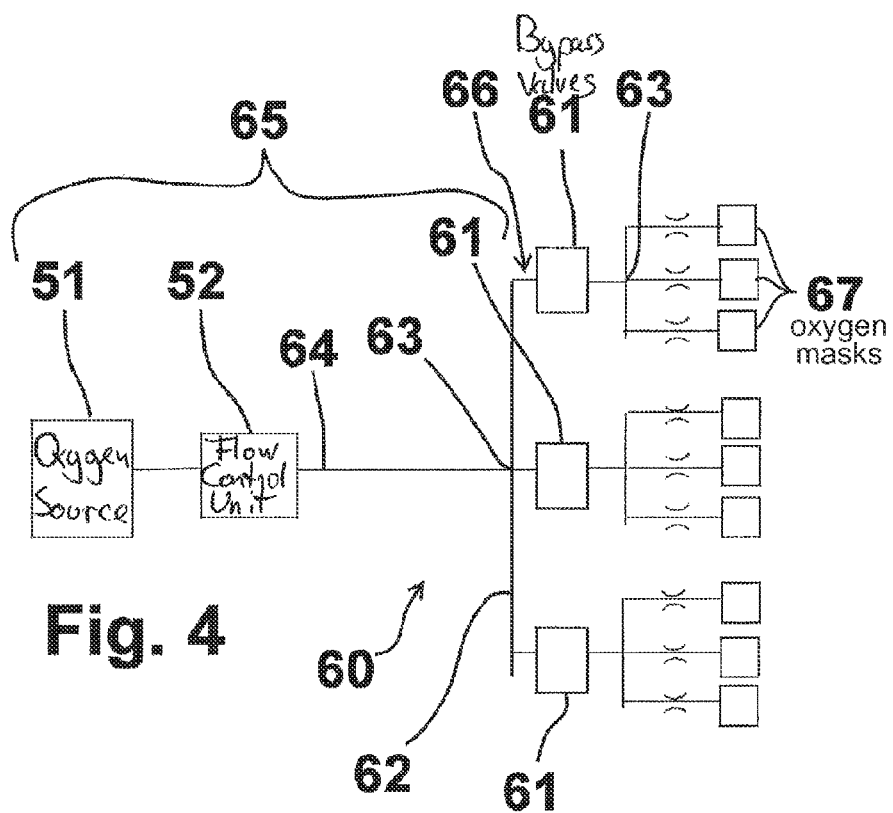
FIG. 4 is a second embodiment of an oxygen breathing device in a schematic view according to the present invention and FIG. 5 is a third embodiment of an oxygen breathing device in a schematic view according to the present invention.

FIG. 4 shows a second embodiment of an oxygen breathing device 60 similar to the oxygen breathing device 50 as shown in FIG. 3. The oxygen breathing device 60 comprises an oxygen source 51, a flow control unit 52 and a number of decentralized bypass valves 61 arranged in a distribution network 62 comprising manifolds 63 that direct oxygen to oxygen masks 67. The bypass valves 61 are supplied with oxygen via an oxygen supply line 64 including a first central oxygen line section 65 and a number of second oxygen line sections 66. The dimensions of the bypass valves 61 are smaller than the dimensions of the bypass valve 53 shown in FIG. 3.

Figure 5:
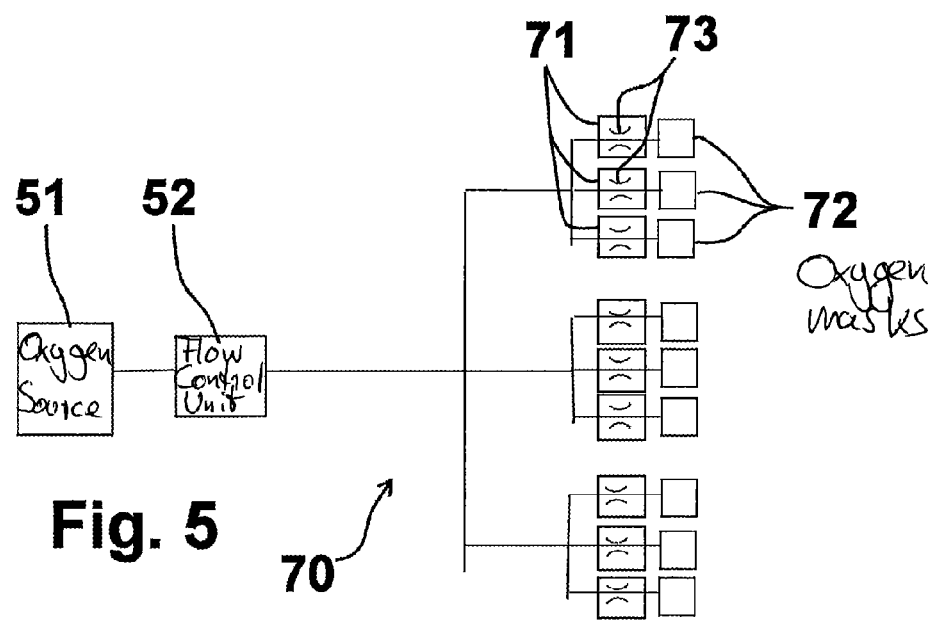

FIG. 5 shows a third embodiment of an oxygen breathing device 70 similar to the oxygen breathing device 60 as shown in FIG. 4. The oxygen breathing device 70 comprises an oxygen source 51, a flow control unit 52 and a plurality of combined bypass valves 71, similar to the bypass valve 30 as depicted in FIG. 2. The combined bypass valves 71 are arranged in oxygen flow direction close to each passenger oxygen supply mask 72. Calibrated orifices 73 for controlling the oxygen flow to the passenger are each integrated in one of the combined bypass valves 71. The dimensions of the bypass valves 71 are smaller than the dimensions of the bypass valves 53 shown in FIG. 3 and bypass valves 61 shown in FIG. 4.

The invention claimed is:

1. An emergency oxygen system for use in an aircraft, the emergency oxygen system comprising:
  (a) an oxygen source, wherein the oxygen source is a chemical oxygen generator or an oxygen pressure tank,
  (b) at least one oxygen mask connected via an oxygen supply line to said oxygen source,
  (c) a flow control unit adapted to receive a signal indicating ambient pressure or to detect ambient pressure and to control a flow of oxygen through the oxygen supply line depending on said ambient pressure, wherein the flow control unit is adapted to:
    provide a low oxygen flow at a first ambient pressure, and
    provide a higher oxygen flow at a second ambient pressure which is lower than said first ambient pressure, and
  (d) at least one bypass valve arranged in the oxygen supply line and comprising a first flow path and a second flow path comprising a bypass channel in a parallel flow arrangement to said first flow path, wherein each of said at least one bypass valves is adapted to:
    direct the flow of oxygen through said first flow path at an ambient pressure above a predetermined level according to a first flow condition,
    direct the flow of oxygen through said second flow path at an ambient pressure below a predetermined level according to a second flow condition, and
    wherein said first flow path has a smaller flow cross section than said second flow path, and
    wherein the oxygen source, the flow control unit, and the at least one bypass valve are in a serial flow arrangement along the oxygen supply line.

2. The emergency oxygen system according to claim 1, wherein said first flow path comprises a calibrated orifice.

3. The emergency oxygen system according to claim 1, wherein said first flow path consists of a flow through a calibrated orifice only and said second flow path consists of a flow through said bypass channel only or through both said bypass channel and said calibrated orifice.

4. The emergency oxygen system according to claim 1, wherein
  each of said at least one bypass valves comprises a first flow channel comprising an orifice with a predetermined cross-section and a second flow channel, wherein a spring biased valve member engages a valve seat and a pressure inside the oxygen supply line acting against said spring biased valve member to switch the spring biased valve member to switch each of the at least one bypass valves between said first and second flow condition.

5. The emergency oxygen system according to claim 1, wherein:
  a plurality of oxygen masks are connected to said oxygen source via a manifold,
  the oxygen supply line comprises a first central oxygen line section directing oxygen from the oxygen source to said manifold and a plurality of second oxygen line sections each directing oxygen from the manifold to an oxygen mask, and
  each of said at least one bypass valves is arranged in a flow direction between said flow control unit and said oxygen masks.

6. The emergency oxygen system according to claim 1, wherein:
  each of said at least one bypass valves is arranged in a first central oxygen line section in a flow direction between said flow control unit and said manifold.

7. The emergency oxygen system according to claim 5, wherein the at least one bypass valve comprises a plurality of bypass valves, wherein at least a number of said plurality of second oxygen line sections comprises one of said plurality of bypass valves.

8. The emergency oxygen system according to claim 1, wherein
  each of said at least one bypass valves comprises a first and a second calibrated orifice, said second calibrated orifice having a larger flow cross section than said first calibrated orifice, and wherein:
  in said first flow condition the flow of oxygen is flowing through said first calibrated orifice; and
  in said second flow condition the flow of oxygen is at least partially circumventing said first calibrated orifice and is flowing through said second calibrated orifice.

9. The emergency oxygen system according to claim 8, wherein
in said second flow condition a first part of the flow of oxygen is flowing through said first calibrated orifice and a second part of the flow of oxygen is flowing through a bypass line arranged in parallel to said first calibrated orifice.

10. The emergency oxygen system according to claim 8, wherein
in said first flow condition the flow of oxygen is flowing through said first and second calibrated orifices in a serial arrangement.

11. The emergency oxygen system according to claim 1, wherein each of said at least one bypass valves comprises:
a housing having an inlet opening and an outlet opening,
a first flow channel connecting said inlet opening and said outlet opening,
a second flow channel connecting said inlet opening and said outlet opening,
a valve piston sealing against a valve seat inside said housing,
wherein, when said valve piston is in sealing contact to said valve seat, the second flow channel is interrupted thus requiring oxygen flowing through each of the at least one bypass valve from the inlet to the outlet opening to flow through said first flow channel, and
wherein, when said valve piston is in a distance position without contact to said valve seat, the second flow channel is open thus allowing oxygen flowing through each of the at least one bypass valves from the inlet to the outlet opening to flow through said first and said second flow channel.

12. The emergency oxygen system according to claim 11, wherein:
a first calibrated orifice is arranged in the first flow channel, and
a second calibrated orifice is arranged in the second flow channel,
wherein said first calibrated orifice has a smaller flow cross section than said second calibrated orifice.

13. The emergency oxygen system according to claim 11, wherein:
said piston is hollow,
the first and second flow channel extend through said piston and
said second calibrated orifice is arranged in the piston.

14. A method for providing oxygen to a passenger of an aircraft, comprising the steps of:
providing oxygen from an oxygen source to at least one oxygen mask,
automatically controlling a flow of the oxygen by a flow control unit by:
(a) receiving a signal indicating ambient pressure or detecting ambient pressure; and
(b) controlling the flow of the oxygen through an oxygen supply line depending on said ambient pressure, in that a low oxygen flow is provided at a first ambient pressure, and a higher oxygen flow is provided at a second ambient pressure which is lower than said first ambient pressure, and
directing the oxygen from said flow control unit to said oxygen mask via a bypass valve arranged in a serial flow arrangement along the oxygen supply line with the flow control unit, the bypass valve comprising a first flow path and a second flow path comprising a bypass channel in a parallel flow arrangement to said first flow path, wherein said first flow path has a smaller cross section than said second flow path and wherein said bypass valve:
(a) directs the flow of the oxygen through said first flow path at an ambient pressure above a predetermined level according to a first flow condition, and
(b) directs the flow of the oxygen through said second flow path at an ambient pressure below a predetermined level according to a second flow condition.

15. A method for maintaining an emergency oxygen system of an aircraft, said emergency oxygen system comprising:
installing an oxygen source comprising a chemical oxygen generator or an oxygen pressure tank,
installing at least one oxygen mask connected via an oxygen supply line to said oxygen source,
installing a flow control unit in a serial flow arrangement with said oxygen source along the oxygen supply line, wherein said flow control unit is adapted to receive a signal indicating ambient pressure or to detect ambient pressure and to control a flow of oxygen through the oxygen supply line depending on said ambient pressure, wherein the flow control unit is adapted to:
(a) provide a low oxygen flow at a first ambient pressure,
(b) provide a higher oxygen flow at a second ambient pressure which is lower than said first ambient pressure, and
(c) to increase said flow of oxygen in at least two steps, and
installing a bypass valve in a serial arrangement with said flow control unit along the oxygen supply line, said bypass valve comprising a first flow path and a second flow path comprising a bypass channel in a parallel flow arrangement to said first flow path, wherein said bypass valve is adapted to:
(a) direct the flow of oxygen through said first flow path at an ambient pressure above a predetermined level according to a first flow condition, and
(b) direct the flow of oxygen through said second flow path at an ambient pressure below a predetermined level according to a second flow condition,
(c) wherein said first flow path has a smaller flow cross section than said second flow path.

16. The emergency oxygen system of claim 1, wherein the at least one oxygen mask comprises a plurality of oxygen masks and wherein the emergency oxygen system further comprises a first manifold that distributes the flow of oxygen from the at least one bypass valve to a plurality of second manifolds, and
wherein each of the plurality of second manifolds distributes the flow of oxygen from the first manifold to a subset of the plurality of oxygen masks,
wherein the oxygen supply line comprises a plurality of individual oxygen supply line sections, and
wherein each of the individual oxygen supply line sections connects one of the oxygen masks of the subset of the plurality of oxygen masks with one of the plurality of second manifolds and wherein each of the individual oxygen supply line sections comprises a restrictor.

17. The emergency oxygen system of claim 1, wherein the at least one oxygen mask comprises a plurality of oxygen masks, wherein the at least one bypass valve comprises a plurality of bypass valves and wherein the emergency oxygen system further comprises:
a first manifold that distributes the flow of oxygen from the flow control unit to the plurality of bypass valves;
a plurality of second manifolds, wherein each of the plurality of second manifolds distributes the flow of oxygen from one of the plurality of bypass valves to a subset of the plurality of oxygen masks;

wherein the oxygen supply line comprises a plurality of individual oxygen supply line sections; and wherein each of the individual oxygen supply line sections connects one of the oxygen masks of the subset of the plurality of oxygen masks with one of the plurality of second manifolds and wherein each of the individual oxygen supply line sections comprises a restrictor.

18. The emergency oxygen system of claim 1, wherein the at least one oxygen mask comprises a plurality of oxygen masks, wherein the at least one bypass valve comprises a plurality of bypass valves and wherein the emergency oxygen system further comprises:

a first manifold that distributes the flow of oxygen from the flow control unit to a plurality of second manifolds;

wherein each of the plurality of second manifolds distributes the flow of oxygen from the first manifold to a subset of the plurality of bypass valves;

wherein each of the bypass valves of the subset of the plurality of bypass valves delivers the flow of oxygen to one of the plurality of oxygen masks via an individual oxygen supply line section of the oxygen supply line; and wherein a restrictor is integrated into each of the plurality of bypass valves.

* * * * *

UNITED STATES PATENT AND TRADEMARK OFFICE
CERTIFICATE OF CORRECTION

PATENT NO. : 9,119,976 B2  
APPLICATION NO. : 13/542803  
DATED : September 1, 2015  
INVENTOR(S) : Wolfgang Rittner and Rudiger Meckes Page 1 of 1

It is certified that error appears in the above-identified patent and that said Letters Patent is hereby corrected as shown below:

In the Claims

In Column 9, line 26, delete "valve" and insert --valves-- therefor.

Signed and Sealed this
Third Day of May, 2016

Michelle K. Lee
*Director of the United States Patent and Trademark Office*